United States Patent
Patterson et al.

[19]

[11] Patent Number: 5,978,087
[45] Date of Patent: Nov. 2, 1999

[54] OPTICAL COLLECTOR HEAD ETC

[75] Inventors: Eann Alexander Patterson; Zhi Fan Wang, both of Sheffield, United Kingdom

[73] Assignee: The University of Sheffield, Sheffield, United Kingdom

[21] Appl. No.: 08/973,349

[22] PCT Filed: Jul. 12, 1996

[86] PCT No.: PCT/GB96/01666

§ 371 Date: Dec. 5, 1997

§ 102(e) Date: Dec. 5, 1997

[87] PCT Pub. No.: WO97/04300

PCT Pub. Date: Feb. 6, 1997

[30] Foreign Application Priority Data

Jul. 14, 1995 [GB] United Kingdom ............... 9514487

[51] Int. Cl.$^6$ ............. G01B 11/06; G01B 11/16
[52] U.S. Cl. .................................. 356/369; 356/33
[58] Field of Search ................ 356/33, 369; 73/800

[56] References Cited

U.S. PATENT DOCUMENTS

| | | | |
|---|---|---|---|
| 3,589,821 | 6/1971 | Robert et al. .................. | 356/33 |
| 3,658,405 | 4/1972 | Pluta ............................ | 350/12 |
| 3,902,805 | 9/1975 | Redner ......................... | 250/225 |
| 4,781,455 | 11/1988 | Machler et al. ............... | 356/34 |
| 4,850,711 | 7/1989 | Sano et al. .................... | 356/369 |
| 4,904,085 | 2/1990 | Spillman, Jr. et al. ......... | 356/364 |
| 5,073,025 | 12/1991 | Brooks . | |
| 5,164,587 | 11/1992 | Caimi et al. .................. | 250/227.17 |
| 5,311,285 | 5/1994 | Oshige et al. ................. | 356/367 |
| 5,335,066 | 8/1994 | Yamada et al. ............... | 356/367 |

FOREIGN PATENT DOCUMENTS

| | | |
|---|---|---|
| 0300508 | 1/1989 | European Pat. Off. . |
| 0553460 | 4/1993 | European Pat. Off. . |

*Primary Examiner*—Robert H. Kim
*Assistant Examiner*—Zandra V. Smith
*Attorney, Agent, or Firm*—Trexler, Bushnell, Giangiorgi & Blackstone, Ltd.

[57] ABSTRACT

An optical collector head comprises a beam splitting device (5) capable of producing at least three output beams (9) in different directions; a single objective lens (4) to provide a collimated beam to the beam splitting device (5); and an assembly of: (a) a quarter wave plate (6), or plate producing a similar effect; (b) a polarizer acting as an analyzing element; (c) a lens; and (d) a recording device (3/1, 3/2, 3/4) for the simultaneous capture of phase-stepped images from each output beam. The invention also includes a polarimetric device comprising an optical collector head as defined above and a source (12) of polarized light; and a polarimetric device comprising an optical collector head as defined above and a source (12) of polarized light.

20 Claims, 6 Drawing Sheets

OPTICAL COLLECTOR HEAD ETC

FIELD OF THE INVENTION

This invention relates to an optical collector head, a stress analysis device, and to a reflection polariscope for strain analysis of a component. Typical uses are in the aeronautical or automobile industries, to facilitate strain analysis of real components, applicability for crack detection; operation for static, dynamic and cyclic events; and provision for full-field principal strain data.

DESCRIPTION OF PRIOR ART

In Strain 27(2):49–56, 1991, is an Article by E. A. Patterson and Z. F. Wang entitled "Towards full field automated photoelastic analysis of complex components" is described a technique for the sequential capture of images.

SUMMARY OF THE INVENTION

According to a first aspect of the present invention there is provided an optical collector head comprising:

An optical collector head comprising:
  (i) a beam splitting device capable of producing at least three output beams in different directions;
  (ii) a single objective lense to provide a collimated, or substantially collimated, beam to the beam splitting device and, for each output beam
  (iii) an assembly of:
    (a) a quarter wave plate, or plate producing a similar effect;
    (b) a polarizer acting as an analyzing element;
    (c) a lens, and
    (d) a recording device for the simultaneous capture of phase-stepped images from each output beam, with each output beam having different orientations of the quarter wave plate, or plate producing a similar effect and of the polarizer.

According to a second aspect of the invention, there is provided a polarimetric device for stress or chemical analysis comprising an optical collector head as defined above and a source of polarised light.

According to a third aspect of the invention there is provided a reflection polariscope comprising an optical collection head as defined above and a source of polarized light.

PREFERRED FEATURES OF THE INVENTION

Preferably, the beam splitting device is capable of producing four output beams, preferably of equal intensity, whilst the recording device is preferably a CCD (charge coupled device) camera.

Whilst the beam splitting device could consist of a mirror system, preferably the beam splitting device consists of three cube beam splitters, preferably with a 50/50 splitting ratio. It is also preferred to provide each assembly with a band width filter.

From the practical viewpoint alignment and focusing of the recording devices is much simplified if, in accordance with another preferred feature, the optical components and recording devices are mounted on a machined optical bench.

With the device of the second aspect, the object to be examined, e.g. in chemical analysis, may itself have a polarized light source.

With the third aspect, the polariscope, the light source is conveniently a quartz tungsten hallogen lamp, e.g. of 100 W, and may be used in a reflective mode or a direct mode.

The optical collector head in accordance with the first aspect of the invention produces monochromatic images that are registered by a recording device. The images are phase-stepped and allow the relative retardation and isoclinic angle to be evaluated for the object being viewed. Subsequent data processing allows the relative retardation to be converted from a periodic map to a continuous map of isochromatic fringe order, but a calibration at two points is required to produce unambiguously a map of absolute isochromatic fringe order. This calibration is provided manually by the operator and is thus potentially subject to error. However, recent research has shown that the spectral contents of the polarized light can be used to determine the absolute isochromatic fringe order when a white light source is used, but measurement of the spectral contents over the entire field of an image is limited by the lack of availability of devices capable of measuring simultaneously multiple-wavelength spectral at many spatial points (e.g. 65,536 in a 256×256 array), whilst scanning devices are limited by the speed of processing. It has been shown that 8 wavelengths are sufficient to allow absolute fringe orders up to approximately 6 to be measured reliably.

According to another feature of the invention, the optical collector head in accordance with the first aspect is provided with a calibration device comprising, for each output of the beam splitting device, a pair of cube beam splitters, the first cube beam splitter, of each pair passing an undeflected beam with each undeflected beam having an identical bandwidth filter, to evaluate the relative retardation and isoclinic angle using phase stepping, and the deflected beam from the first beam splitter to the second beam splitter resulting in an undeflected output and a deflected output with each having a different bandwidth filter to allow a spectrum to be defined, to enable eight simultaneous measurements to be made.

Thus, eight simultaneous measurements can be made using the optical collector head by replacing the three (or four) recording devices by a further pair of cube beamsplitters. The bandwidth filter in the optical collector head should be replaced by three in each assembly. The filters on the undeflected beam need to be identical for all assemblies and these beams are used to evaluate the relative retardation and isoclinic angle as before using phase-stepping. The bandwidth filters on the deflected beams, S should be all different so as to allow a spectrum to be defined. The device in this configuration allows four phase-stepped images to be acquired at a common bandwidth, and eight further images to be acquired at different wavelengths. These later images may also be phase-stepped but this represents no serious difficulty in subsequent data processing which provides both absolute isochromatic fringe order and isoclinic angle for the full field of view. All the images can be recorded simultaneously using one monochromatic recording device for each beam. Alternatively a three-chip device with tuneable bandwidth filters could be used in place of the two additional cube beam splitters.

DETAILED DESCRIPTION OF THE DRAWINGS

Figure 1A:
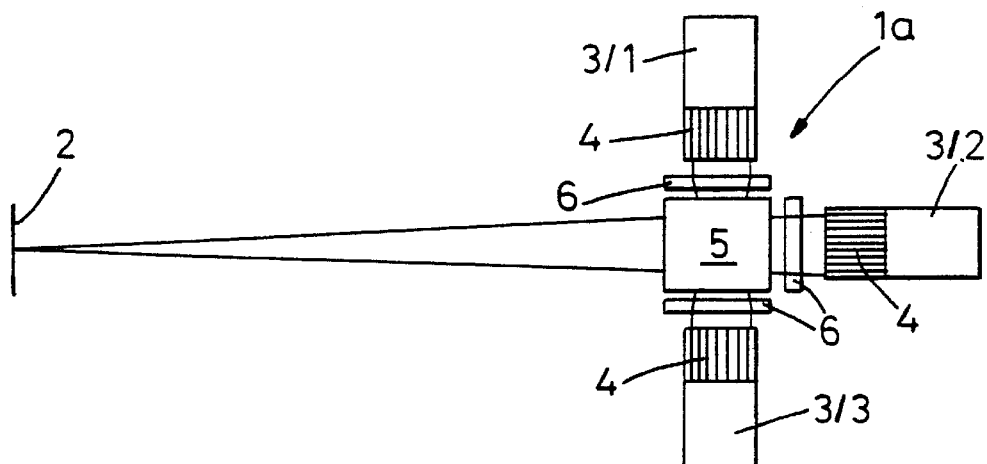
FIGS. 1A, 1B and 1C, are respectively diagrammatic plan views of these embodiments of optical collector head.
Figure 1B:
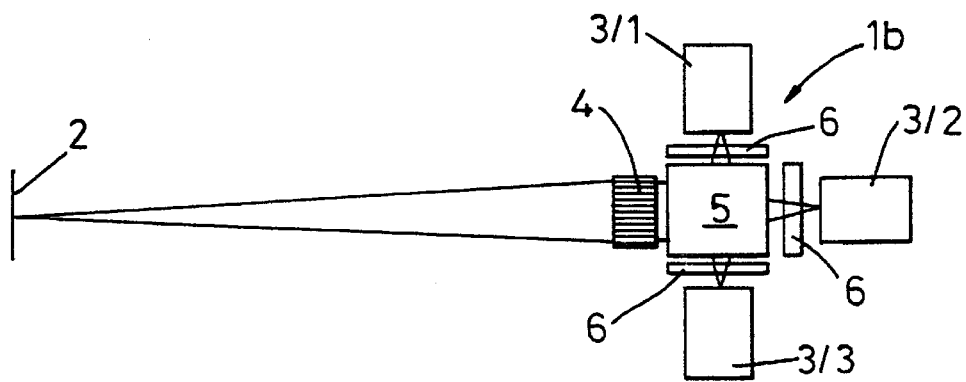
Figure 1C:
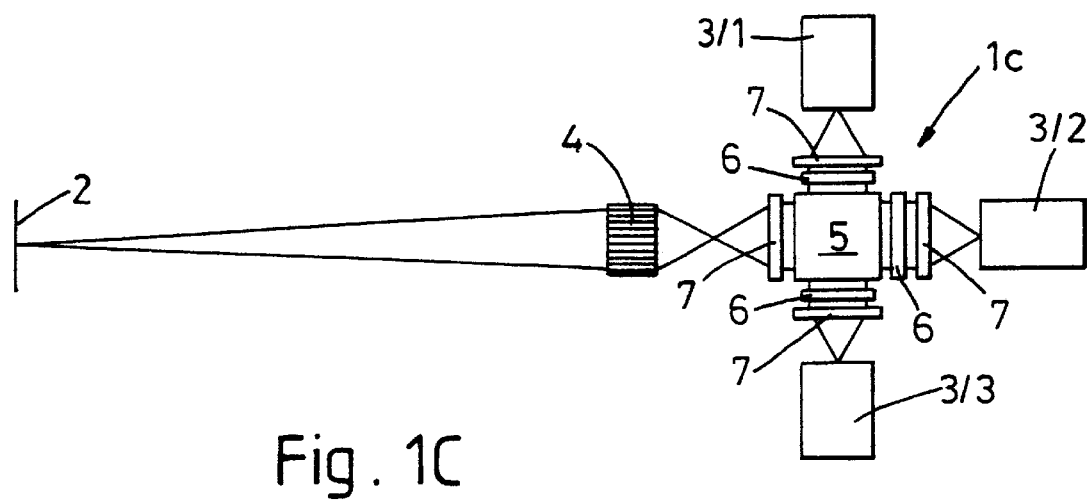

The optical collection heads 1a, 1b and 1c of FIGS. 1A, 1B, and 1C are designed to simultaneously produce four images from a single object 2, with the optical heads being intended in one mode for operational association with a source of polarised light so as to constitute a reflection polariscope.

Figure 5:
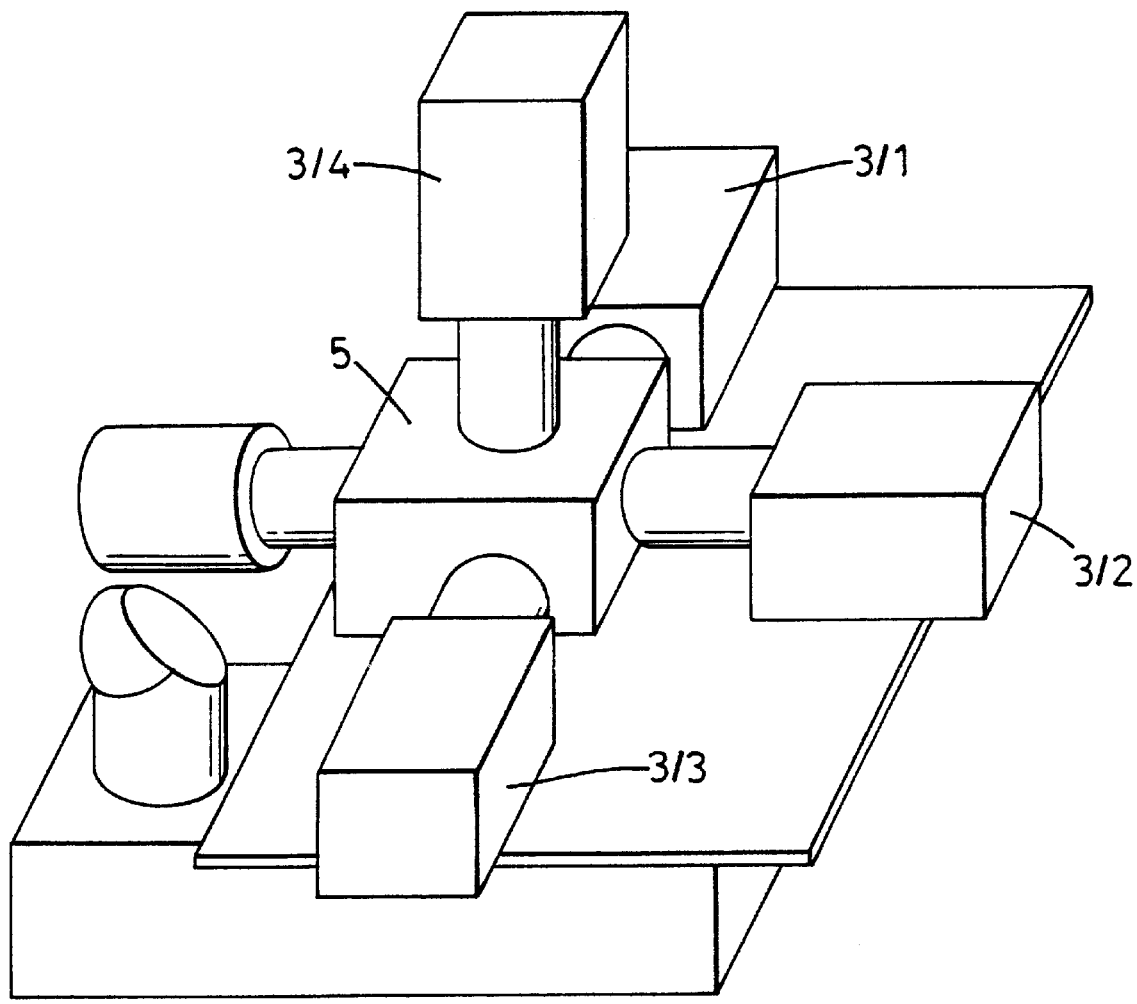
FIG. 5 is a schematic layout of a preferred optical head and light source.

FIG. 1A and 5 show a simple arrangement where four CCD cameras 3/1, 3/2, 3/3 and 3/4 with four objectives 4 were located around a beam-splitting device 5. Quarterwave plates and polarizers 6 (acting as analysers) are inserted and set at different orientations between each objective 4 and the beam-splitting device 5.

FIG. 1B shows a modification of the FIG. 1A configuration, where a single objective 4 was used in front of the beam-splitting device 5. This arrangement simplifies the focusing procedure requirement of the FIG. 1A embodiment. However, since optical components such as the beam-splitting system and the quarterwaves plates have to be inserted between the objective and the cameras, an objective with longer back focal length is required. Therefore, a camera lens must be used with the objective to increase the back focal length, or a different type of objective, such as an enlarger objective, should be used instead.

In the embodiment of FIG. 1C, the beam is collimated with an achromatic lens 7 into a parallel beam which, as with FIGS. 1A and 1B, passes through the beam-splitting device 5, quarterwave plates and the polarizers 6, again set at different orientations. Many combinations of orientation will work, as will be appreciated by persons skilled in the art. The split beams are then re-focused with similar CCTV camera lenses onto each CCD camera. The advantage of this arrangement is that the beam-splitters, quarterwave plates and the analysers are used under near-normal beam incidence. In addition, the distance between lenses is adjustable without the need of any additional optical components.

Figure 2:
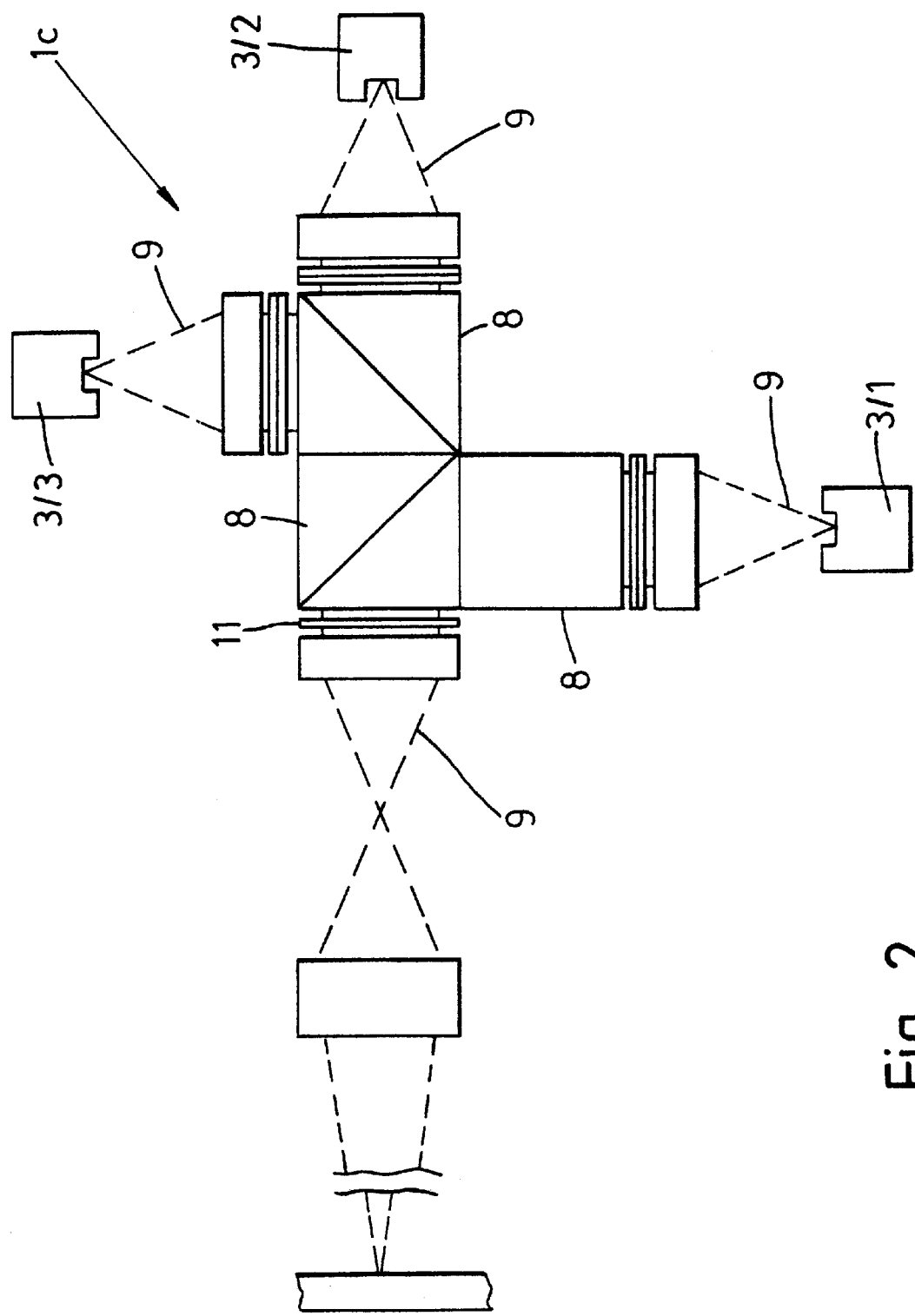
FIG. 2 is a schematic layout of a preferred embodiment of optical collector head.

In FIG. 2, the beam-splitting device is shown to consist of three cube beam-splitters 8 with a 50/50 splitting ratio. They are mounted in such a way that four output beams 9 of equal intensity are produced along four different directions to facilitate mounting of the four cameras 3/1 to 3/4, and with this design the resulting four arms of the optical collection head 1c have similar optical paths, which the focusing of the images is assured by a common camera objective. The design has also taken into account the flexibility of using either CCTV camera lenses or photographic camera lenses. Each arm of the optical collection head 1c thus consists of a quarterwave plate, an analyser, a CCTV lens and a CCD camera. With a common polarised light source, e.g. as detailed in FIG. 4, each arm effectively forms a stand alone polariscope.

Figure 3:
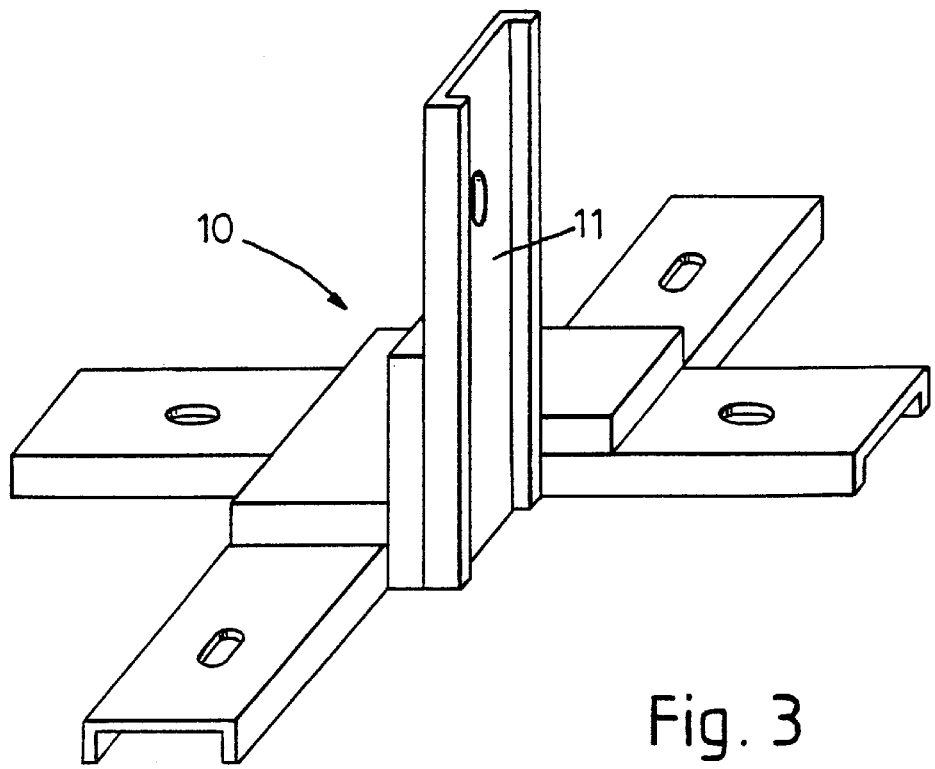
FIG. 3 is an isometric view of an optical bench.

In FIG. 3 is shown an optical-bench 10 also designed to hold all optical components and CCD cameras of the optical collection head. A 10 nm bandwidth filter 11 centered at 580 nm is used to provide a monochromatic picture and to ease the analysis of data and it is desirable that high quality optical components be used to minimise optical aberrations and image distortion.

The four CCD signals from four cameras 3/1 to 3/4 (Panasonic WV BP100) are combined simultaneously into one composite CCD signal with a commercially available device known as a multi-plex unit and supplied by Panasonic (Model No. WJ410), which allows the on-line-display of four images on four quadrants of a monitor screen. The composite CCD signal output of the quad system is then fed into an image digitiser, where the four images are simultaneously captured. Due to the beam-splitting system, three out of four images are reversed. The reversed images must therefore be corrected after being digitised, and conveniently a program is written into the digitiser's own memory to digitally reverse back the reversed images, before the images were sent to the computer for processing and analysis.

Figure 4:
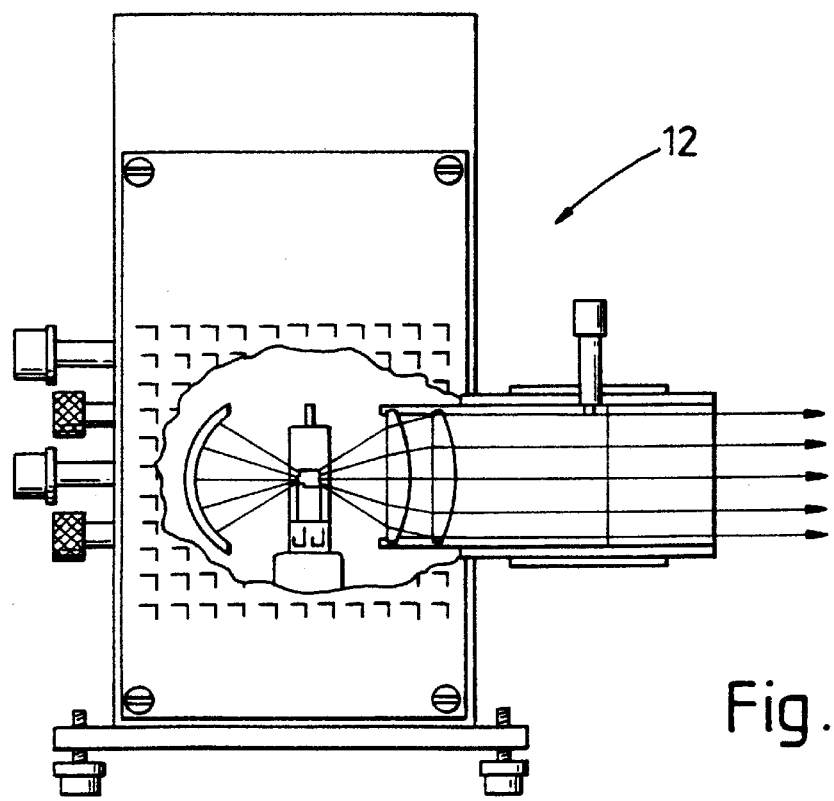
FIG. 4 is a diagrammatic side elevation of a light source and housing.

For medium power ranges, a commercially available light source 12 (Oriel Model No. 66181) illustrated in FIG. 4 can be adopted with some alteration so that the source is situated in a housing adjacent to the optical collection head as shown in FIG. 5. A cold mirror is used in front of the light source to steer the beam and to cut off near infrared radiation at the same time, together with a polariser and a quarterwave plate after the cold mirror, to generate circularly polarised light.

Figure 6:
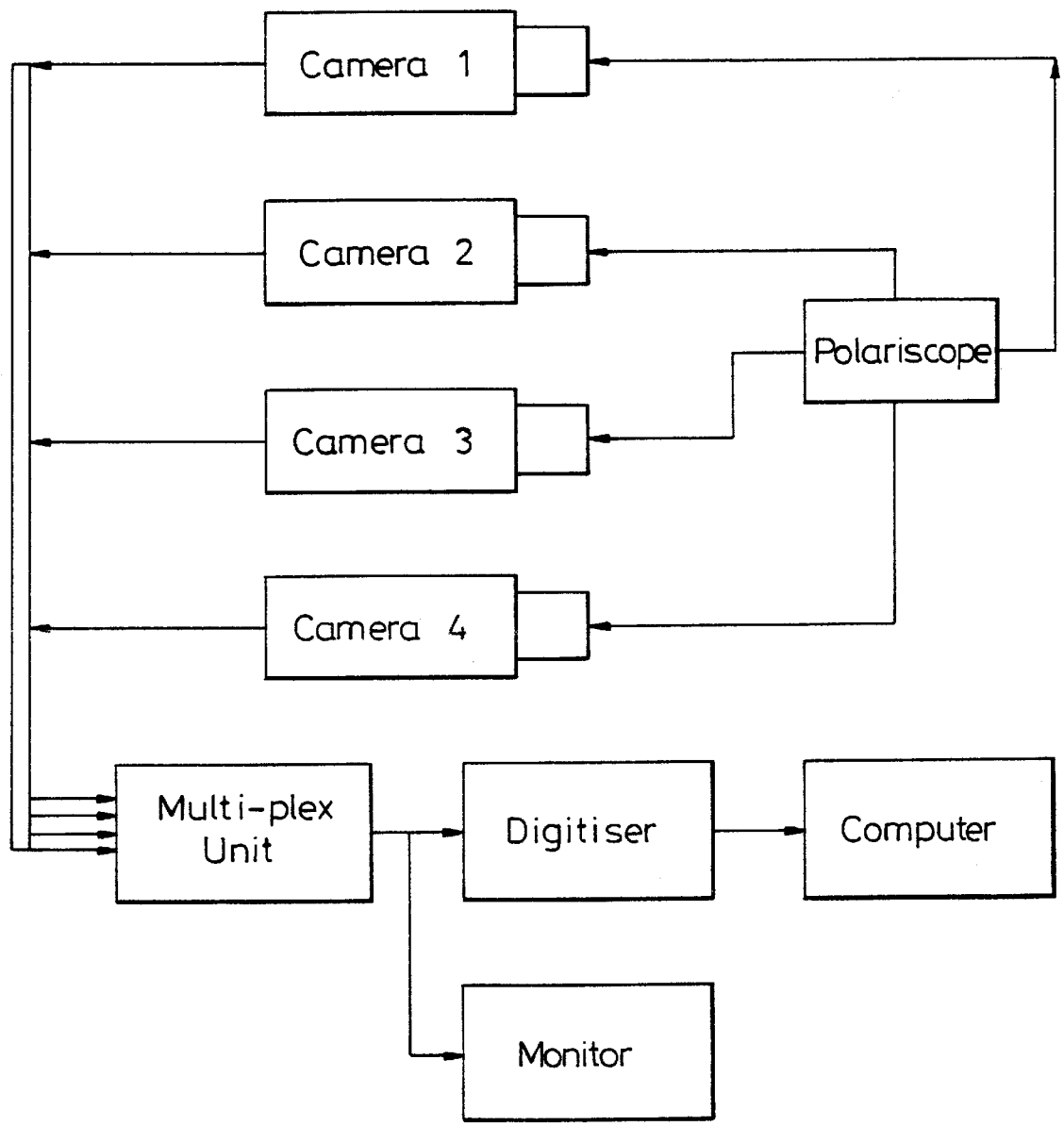
FIG. 6 is a diagram of a hardware configuration for the automated reflection system.

In FIG. 6 is illustrated a transputer-based digitiser and a Multivision Monitor (Taxan 725). The digitiser has four channels available for colour images. A multi-plexer (Panasonic Quad WJ 410) device combines four input signals into a single output signal.

Figure 7:
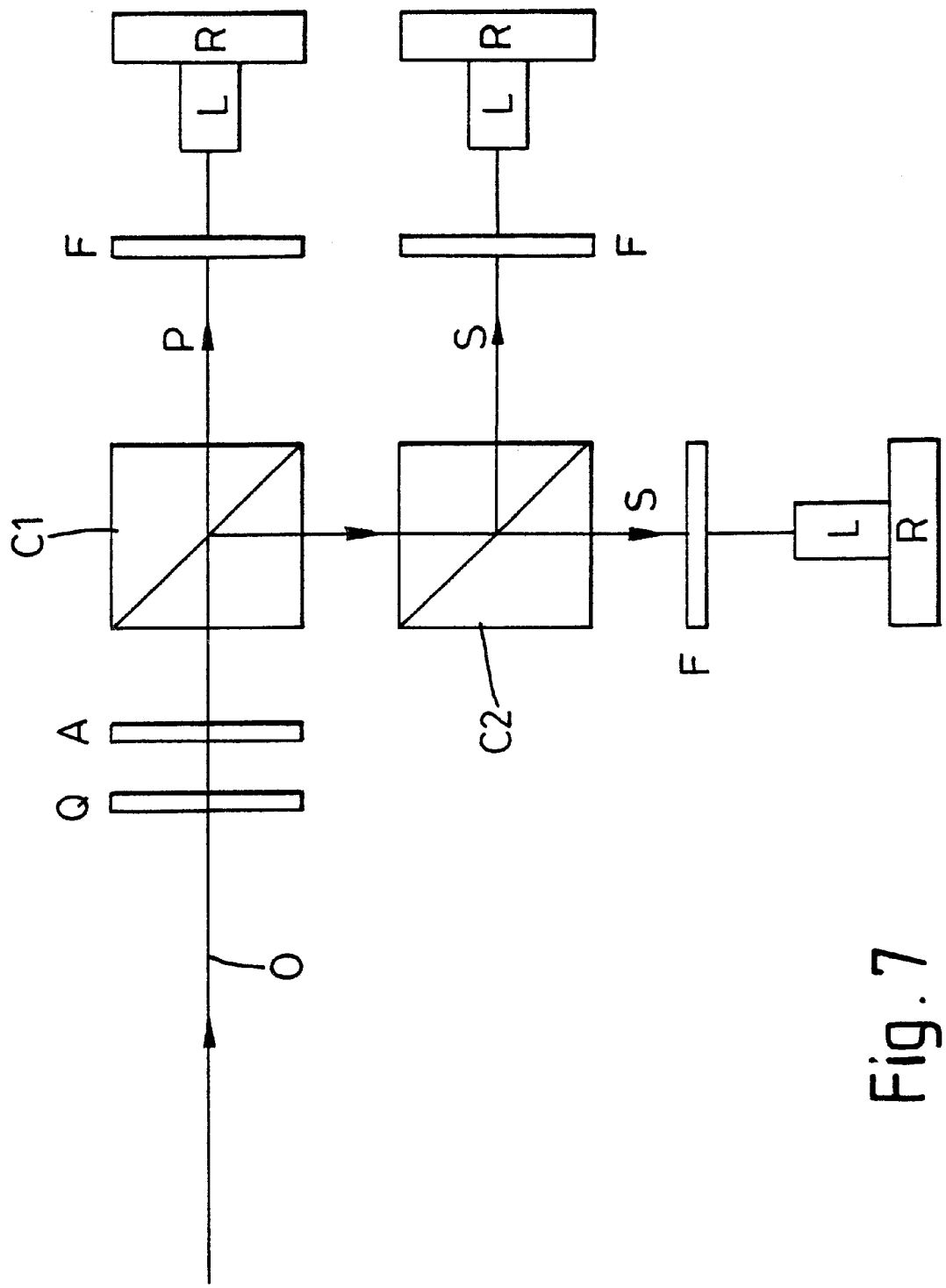
FIG. 7 is a schematic diagram of one of the three (or four) calibration assemblies.

In the assembly illustrated in FIG. 7 (which is used in conjunction with two or three similar assembles associated with the three (or four) outputs of the beam splitting device), a pair of cubes C1 and C2 are provided, with an output O of the optical collector head passing firstly through a quarter waveplate Q and a polarizer acting as an analyser A, before entry into cube C1 which splits the beam into an undeflected beam P, to provide phase stepped image, through a bandwidth filter F, a lense L into a recording device R, all three (or four) filters F being identical. The deflected beam exiting from C1 passes into C2 and exits as undeflected and deflected beams S, these two beams passing through a bandwidth filter F, a lense L into a recording device R, with all three (or four) filters F of the beams S supplying spectral contents images all being different.

We claim:

1. An optical collector head comprising:
    (i) a beam splitting device capable of producing at least three output beams in different directions;
    (ii) at least one objective lens and, for each of said output beams,
    (iii) an assembly of:
        (a) a birefringent plate producing a relative retardation;
        (b) a polarizer acting as an analyzing element;
        (c) a lens; and
        (d) a recording device for the simultaneous capture of phase-stepped images from each of said output beams, with each of said output beams having different orientations of the birefringent plate and of the polarizer, said optical collect head provided with a calibration device comprising, for each of said output beam of said beam splitting device, a pair of cube beam splitters, with the first cube beam splitter of each pair passing an undeflected beam with each undeflected beam having an identical bandwidth filter, to evaluate the relative retardation and isoclinic angle using phase stepping, and the deflected beam passing from the first beam splitter to the second beam splitter resulting in an undeflected output and a deflected output with each having a different bandwidth filter to allow a spectrum to be defined, to enable eight simultaneous measurements to be made.

2. An optical collector head as claimed in claim 1, wherein said birefringent plate is a quarter waver plate.

3. An optical collector head as claimed in claim 1, wherein said beam splitting device is capable of producing four output beams.

4. An optical collector head as claimed in claim 3, wherein said output beams are of equal intensity.

5. An optical collector head as claimed in claim 1, comprising four objective lenses with said recording device comprising four video cameras, arranged around said beam splitting device.

6. An optical collector head as claimed in claim 3, comprising an achromatic lens to effect beam collimation.

7. An optical collector head as claimed in claim 1, wherein a single objective lens is arranged in front of said beam splitting device.

8. An optical collector head as claimed in claim 1, wherein said recording device is a CCTV/CCD camera.

9. An optical collector head as claimed in claim 1, wherein said beam splitting device consists of a mirror system.

10. An optical collector head as claimed in claim 1, wherein said beam splitting device consists of three cube beam splitters.

11. An optical collector head as claimed in claim 10, wherein said cube beam splitters have a 50/50 splitting ratio.

12. An optical collector head as claimed in claim 1, wherein said assembly is provided with a band width filter.

13. An optical collector head as claimed in claim 1, wherein said optical components and recording devices are mounted on a machined optical bench.

14. A polarimetric device for stress or chemical analysis comprising an optical collector head which includes:
 (i) a beam splitting device capable of producing at least three output beams in different directions;
 (ii) at least one objective lens and, for each of said output beams,
 (iii) an assembly of:
  (a) a birefringent plate producing a relative retardation;
  (b) a polarizer acting as an analyzing element;
  (c) a lens; and,
  (d) a recording device for the simultaneous capture of phase-stepped images from each of said output beams, with each of said output beams having different orientations of the birefringent plate and of the polarizer, said optical collector head; provided with a calibration device comprising, for each of said output beam of said beam splitting device, a pair of cube beam splitters, with the first cube beam splitter of each pair passing an undeflected beam with each undeflected beam having an identical bandwidth filter, to evaluate the relative retardation and isoclinic angle using phase stepping, and the deflected beam passing from the first beam splitter to the second beam splitter resulting in an undeflected output and deflected output with each having a different bandwidth filter to allow a spectrum to be defined, to enable eight simultaneous measurements to be made and a source of polarized light.

15. A polarimetric device as claimed in claim 14, wherein the object to be examined itself has a polarized light source.

16. A reflection polariscope comprising an optical collection head which includes:
 (i) a beam splitting device capable of producing at least three output beams in different directions;
 (ii) at least one objective lens and, for each of said output beams,
 (iii) an assembly of:
  (a) a birefringent plate producing a relative retardation;
  (b) a polarizer acting as an analyzing element;
  (c) a lens; and,
  (d) a recording device for the simultaneous capture of phase-stepped images from each of said output beams, with each of said output beams having different orientations of the birefringent plate and of the polarizer, said optical collector head; provided with a calibration device comprising, for each of said output beam of said beam splitting device, a pair of cube beam splitters, with the first cube beam splitter of each pair passing an undeflected beam with each undeflected beam having an identical bandwidth filter, to evaluate the relative retardation and isoclinic angle using phase stepping, and the deflected beam passing from the first beam splitter to the second beam splitter resulting in an undeflected output and deflected output with each having a different bandwidth filter to allow a spectrum to be defined, to enable eight simultaneous measurements to be made; and a source of polarized light.

17. A reflection polariscope as claimed in claim 16, wherein said source of polarized light is a quartz tungsten halogen lamp.

18. A reflection polariscope as claimed in claim 17, wherein said lamp is of 100 W.

19. A reflection polariscope as claimed in claim 17, wherein said lamp is used in a reflective mode.

20. A reflection polariscope as claimed in claim 17, wherein said lamp is used in a direct transmission mode.

* * * * *